United States Patent [19]

Mans

[11] Patent Number: 4,695,550

[45] Date of Patent: Sep. 22, 1987

[54] ATP: POLYNUCLEOTIDE ADENYLYLTRANSFERASE ENZYME AND METHOD OF PREPARATION THEREOF

[75] Inventor: Rusty J. Mans, Gainesville, Fla.

[73] Assignee: University of Florida, Gainesville, Fla.

[21] Appl. No.: 617,596

[22] Filed: Jun. 5, 1984

[51] Int. Cl.[4] ............................................. C12N 9/12
[52] U.S. Cl. ................................... 435/194; 435/814; 435/815
[58] Field of Search ........................................ 435/194

[56] References Cited

PUBLICATIONS

Enzyme Nomenclature 1978; pp. 222-223, Entry 2.7.7.19 (1979).
Walter et al, Biochimica et Biophysica Acta, vol. 217, pp. 72-82 (1970).
Mans et al, Biochimica et Biophysica Acta, vol. 247, pp. 113-121 (1971).
Mans, Biochemical and Biophysical Research Communications, vol. 45, No. 4, pp. 980-983 (1971).

*Primary Examiner*—Lionel M. Shapiro
*Attorney, Agent, or Firm*—Dennis P. Clarke

[57] ABSTRACT

The invention relates to ATP: polynucleotide adenylyltransferase enzyme and a method for its preparation comprising extraction from monocotyledonous plant tissue and chromatographic separation.

31 Claims, No Drawings

ATP: POLYNUCLEOTIDE ADENYLYLTRANSFERASE ENZYME AND METHOD OF PREPARATION THEREOF

BACKGROUND OF THE INVENTION

In 1967, during research involving the purification of DNA-dependent RNA polymerase from homogenate of maize seedlings, two ATP incorporating activities were resolved by chromatography [Stout et al., Biochem. Biophys, Acta. 134, 327 (1967)]. The major activity was identified as containing RNA polymerase. The second enzyme-containing activity catalyzes the sequential addition of AMP (adenylic acid) moieties from ATP (adenosine triphosphate) to the 3'-hydroxyl terminus of ribo- or deoxyribopolymers [Walter et al., Biochem Biophys, Acta. 217, 72–82 (1970); Mans et al., Biochem. Biophys. Acta. 247, 113–121 (1971); Mans, Biochem. and Biophys. Res. Comm., 45, 980–983 (1971); Mans et al., J. Biol. Chem., 250, 3672–78 (1975); Walter et al., Plant Physiol., 56, 821–25 (1975)].

The unique ability of the activity to utilize both ribo- and deoxyribopolymers as acceptor molecules for polyadenylylation render the enzyme commerically desirable as a reagent for the radioactive "tailing", for example, of RNA and DNA molecules in programs and systems involving the molecular cloning of specific viral prokaryotic and eukaryotic gene sequences. The enzyme containing activity isolated from mammalian cells does not have the ability to utilize deoxyoligomers as primer [Mans et al., Life Sciences, 14, 437–445 (1974)].

The disclosures of each of the references cited hereinabove are incorporated herein by reference.

The utilization of the heretofore only partially purified activity suffered from several disadvantages. The presence of significant exonuclease activity in the partially purified preparations limits the length of the poly A sequence of the accumulated product. The presence of traces of endonucleolytic activities randomly cleave high molecular weight RNA primers, resulting in the formation of less than full-length cDNA probes. Significant DNA endonucleolytic activity introduces random single stranded nicks in polydeoxribonucleotide primers resulting in less than full-length, labeled restriction endonuclease fragments. The activity has significant but relatively low activity on deoxyoligomers as compared with the polyadenylylation of RNA primers of comparable length. The enzyme is labile on storage at 4° C. and upon successive freezing and thawing.

It is an object of the present invention to provide in substantially pure form, the ATP; polynucleotide adenylyltransferase enzyme and a method for its isolation and purification.

SUMMARY OF THE INVENTION

The above and other objects of the invention are achieved by providing a novel method for isolating and purifying the substantially pure enzyme ATP: polynucleotide adenylyltransferase. The enzyme is capable of catalyzing the successive addition of adenylic acid moieties from adenosine triphosphate to the 3'-terminal hydroxyl group of ribopolymers and deoxyribopolymers and is substantially free of interfering nuclease activities. The denatured enzyme exhibits three protein staining bands after polyacrylamide gel electrophoresis with apparent molecular weights (±5%) of 110,000, 93,000 and 71,000 daltons. Glycerol gradient centrifugation and gel exclusion chromatography show that a major polyadenylating activity is associated with the smallest protein.

The method of the invention for producing the ATP enzyme in substantially pure form comprises:

(a) homogenizing monocotyledonous plant tissue in an aqueous medium buffered to a mildly alkaline pH, optimally about pH 8, to solubilize the enzyme and separating insoluble material from solution;

(b) dissolving in the aqueous solution obtained in step (a) the minimum amount of soluble, inert salt necessary to precipitate substantially all of the enzyme and separating precipitated enzyme from the solution;

(c) dissolving the precipitated enzyme from step (b) in an aqueous medium buffered to a mildly alkaline pH, optimally about pH 8;

(d) removing from the solution produced in step (c) any low molecular weight cellular components dissolved therein and adjusting the inert salt ionic strength thereof to from about 0.45M to about 0.75M, optimally to 0.6M;

(e) contacting the solution from step (d) with a weak anion exchange resin whereby nucleic acids, completing enzymic activities and proteinaceous impurities are chromatographically adsorbed thereby to the exclusion of the ATP enzyme;

(f) isolating the ATP enzyme of step (e) following the chromatographic separation, dissolving the enzyme in an aqueous medium buffered to a mildly alkaline pH, optimally to pH 8, and adjusting the inert salt ionic strength thereof to from about 30 mM to about 75 mM, optimally to 50 mM;

(g) contacting the solution of step (f) with a weak anion exchange resin whereby the ATP enzyme is chromatographically adsorbed thereby to the exclusion of proteinaceous impurities;

(h) eluting the adsorbed enzyme from the resin and dialyzing the eluted fraction step (g) against an aqueous solution buffered to a mildly acid pH, optimally to pH 6, and having an ionic strength of dissolved inert salt of from about 10 mM to about 30 mM, optimally to 20 mM;

(i) contacting the dialyzed fraction with a weak cation exchange resin to chromatographically adsorb the ATP enzyme to the exclusion of proteinaceous impurities from which the adsorbed enzyme is separated after elution from the weak cation exchange resin with an aqueous medium buffered to a mildly acid pH, optimally to pH 6, and having an inert salt ionic strength of from about 50 mM to about 200 mM, optimally 150 mM;

(j) contacting the eluted fraction with a polynucleotide covalently bound to an inert matrix to chromatographically adsorb therefrom the ATP enzyme to the exclusion of proteinaceous impurities from which the adsorbed enzyme is separated after elution from the bound polynucleotide with an aqueous medium buffered to an alkaline pH, optimally of pH 8.5, and having an inert salt ionic strength of from about 50 mM to about 200 mM, optimally 150 mM.

DETAILED DESCRIPTION OF THE INVENTION

In order to obtain the substantially pure enzyme of the invention which is absolutely primer dependent and essentially free of interfering nuclease and other activities and which is capable of catalyzing the controlled successive addition of adenylic acid moieties from ATP to the 3'-terminal hydroxyl group of both ribo- and deoxyribopolymers, it is critical that the above-described steps be carried out in the sequence noted.

The enzyme is believed to be comprised of a plurality of peptides, the presence of all of which are necessary to enable the enzyme to catalyze the polyadenylylation of RNA and DNA polymers. The omission, variance or reversal of any of the above-noted sequential steps or the substantial modification of the concentration of any of the reagents results in the removal or inactivation of one or more of the peptide components of the enzyme and an attendant destruction of the activity of the enzyme.

The method of the invention is designed to isolate the enzyme by sequentially removing plant tissue matter, low molecular weight metabolic intermediates, starch and lipids, nucleic acids and proteinaceous impurities in a sequence which will preserve the enzyme. Principally, the method of the invention increases the amount of enzyme prepared per batch, stabilizes the active enzyme to repeated cycles of freezing and thawing and enables the removal of interfering proteinaceous impurities present in the ATP; polynucleotide adenylytransferase fraction prepared according to the partial purification methods of the prior art noted above. The pure enzyme of the present invention is free of the contaminating activity associated with the prior art partially purified product which cleaved the added adenylic acid residues from the ribo- and deoxyribopolymers. The enzyme of the invention is also free of the contaminants in the prior art preparations which cleaves the ribo- and deoxyribopolymer.

By following the method of the invention as described above there is produced a novel and heretofore unavailable enzyme which renders it possible to "tail" both a ribo- and a deoxyribopolymer with a polyadenylic acid sequence of any desired length such that the polymer is unaltered other than the addition of the polyadenylic acid sequence at its 3'-hydroxyl terminus.

Any monocotyledonous plant tissue may be employed in the practice of the invention. It is preferred to employ young shoots of the graminaceous plants. Most preferably, young (4- to 5-day old) corn shoots (2 to 5 cm long), free or roots and kernels, are employed as the source material for the enzyme. Advantageously, the young shoots are harvested and stored frozen to facilitate the isolation of pure enzyme without the necessity for first growing the shoots. It has been determined that pure enzyme can be isolated from shoots which have remained frozen at $-76°$ C. for up to two years.

Preferably, the frozen shoots are thawed and homogenized simultaneously in an aqueous medium buffered o pH 7.8 to 8.2 by the presence therein of Tris.HCl in a concentration of about 50 to 200 mM (optimally of 100 mM). The reducing agent present therein may be any such agent which inhibits the auto-oxidation of lignins and phenolic compounds derived from the plant tissue to products which adversely affect the activity of the enzyme. A suitable such reducing agent is 2-mercaptoethanol, present in the medium at a concentration of from about 25 mM to 70 mM, optimally at 50 mM.

It is also necessary to include in the medium a chelator for heavy metals which deleteriously affect the active enzyme. A suitable such chelator is ethylenediaminetetraacetic acid [EDTA], present therein in a concentration of from about 0.05 mM to about 0.25 mM, optimally 0.1 mM.

It is also necessary to include an inhibitor of proteolytic enzyme activity in order to preserve the stability of the enzyme. A suitable such protease inhibitor is phenylmethylsulfonylfluoride [PMSF], present in the medium at a concentration of from about 0.5 mM to about 3 mM, optimally 1 mM.

It is also preferably but not mandatory to include from about 5% to 10%, by volume, of glycerol in the medium which functions as an anti-freeze and enables the utilization of low temperatures in subsequent operations. The presence of glycerol also facilitates homogenization and several of the subsequent removal procedures.

The homogenization step disrupts the tissue material to maximize cell lysis of thawing and thus releases the active enzyme as a soluble component. The homogenate is subsequently freed of all insoluble material by successive filtration and centrifugation. It is necessary to again bring the supernatant fluid to about 1 mM PMSF to replace the protease inhibitor dissipated in the previous steps.

The homogenization step acts to disrupt the cellulose tissue material and release the active enzyme material. The homogenizate is subsequently freed of all insoluble material by filtration and/or centrifugation.

The supernatant fluid containing dissolved enzyme and impurities is then brought to the minimum concentration of soluble inert salt, preferably, $(NH_4)_2SO_4$, necessary to maximally precipitate all of the active enzyme therefrom. It is preferred to add to the aqueous solution of enzyme a saturated solution of ammonium sulfate to bring the concentration of $(NH_4)_2SO_4$ therein to about 35% to 55%, optimally 50%, by weight. It is essential that both the aqueous solution of the enzyme and the saturated solution of ammonium sulfate be at pH 7.8 to 8.2 prior to mixing. This step effects the precipitation of the active enzyme and some proteinaceous impurities while leaving in solution a plurality of interfering impurities. The precipitate containing the active enzyme is preferably removed from the medium by sequential filtration and centrifugation and dissolved in an aqueous medium buffered to pH 8 and containing a suitable reducing agent, chelating agent and protease inhibitor.

The aqueous medium of this step preferably contains 5 to 25 mM, optimally 10 mM Tris.HCl (pH 8), 1 mM 2-mercaptoethanol (reducing agent), 0.1 mM EDTA (chelator), 1 to 3 mM PMSF and optimally, 5%, by volume, glycerol. The solution containing dissolved enzyme may then be clarified by centrifugation to remove any undissolved matter.

The solution is then treated to remove excess precipitant salt (e.g., $(NH_4)SO_4$) and any dissolved low molecular weight (i.e., <100,000) cellular components dissolved therein. This step contemplates the removal of the noted impurities and simultaneous reduction in the concentration of the precipitant salt. It is critically necessary that the precipitant be replaced with a suitable concentration of inert salt since the active enzyme is unstable and dissociates in the absence of a minmum concentration of salt. Preferably, the removal of low molecular weight components and the reduction in salt concentration operations are effected by exclusion chromatography on a dextran gel (e.g., Sephadex G 100) column which has been previously equilibrated and eluted with an aqueous medium buffered to pH 8 (i.e., 10 mM Tris. HCl) containing reducing agent (i.e., 0.5 to 2 mM 2-mercaptoethanol), chelator (i.e., 0.1 to 0.25 mM EDTA), 150 to 250 mM (optimally 200 mM) divalent salt (i.e., $(NH_4)_2SO_4$) and optimally 5%, by weight, of glycerol.

The excluded salt concentration adjusted solution containing dissolved active enzyme is then preferably pumped directly to a chromatographic column comprising diethylaminoethyl-cellulose (DEAE) which adsorbs many of the nucleic acids and protein contaminants and several of the ATP utilizing enzymes to the exclusion of the active enzyme.

A first fraction of non-adsorbed active enzyme is washed from the DEAE column with a suitable medium buffered to pH 8 (i.e., 5 to 10 mM Tris.HCl) and containing reducing agent (i.e., 1 to 2 mM 2-mercaptoethanol), chelator (i.e., 0.1 to 0.25 mM EDTA), 50 to 250, optimally, 200 mM divalent salt (i.e., $(NH_4)_2SO_4$) and, optimally 5%, by volume, glycerol.

The active enzyme and additional unadsorbed proteins eluted from the DEAE column are then brought to the minimum concentration of soluble inert salt necessary to maximally precipitate all of the active enzyme therefrom. It is preferred to add to the aqueous solution of enzyme crystalline ammonium sulfate to bring the concentration of $(NH_4)_2SO_4$ therein to about 30 to 50% saturation (40% optimally), by weight. This step effects the precipitation of the active enzyme and some proteinaceous impurities while leaving in solution a plurality of interfering impurities. The mixture of precipitated enzyme and impurities is stored frozen to facilitate the isolation of large quantities of pure enzyme from a pooled source.

Upon the accumulation of sufficient material, the frozen slurry is thawed, brought to 1 mM PMSF and the precipitate separated from the aqueous medium by centrifugation.

The solution is then treated to remove the precipitant salt (e.g., $(NH_4)_2SO_4$) and any dissolved low molecular weight (i.e., <15,000) cellular components dissolved therein. This step contemplates removal of the noted impurities and simultaneous replacement of the precipitant salt with a soluble inert salt. It is critically necessary that the precipitant be replaced with a suitable concentration of monovalent salt since the active enzyme is unstable and degrades in the absence of a minimum concentration of salt. Preferably, the removal and salt replacement operations are effected by exclusion chromatography on a dextran gel (e.g., Sephadex G 50) column which has been previously equilibrated and eluted with an aqueous medium buffered to pH 8 (i.e., 5 to 10 mM Tris.HCl) containing reducing agent (i.e., 1 to 2 mM 2-mercaptoethanol), chelator (i.e., 0.1 to 0.25 mM EDTA), 20 to 75 mM, optimally, 50 mM of monovalent salt (i.e. KCl) and, optimally 5%, by volume, of glycerol.

The excluded salt concentration adjusted solution containing dissolved active enzyme is then preferably pumped directly to a chromatographic column comprising diethylaminoethyl-cellulose [DEAE] which adsorbs the active enzyme to the exclusion of certain mostly proteinaceous impurities.

A fraction containing the ATP enzyme is eluted from the DEAE column with a suitable medium buffered to pH 8 (i.e., 5 to 10 mM Tris·HCl) and containing reducing agent (i.e., 1 to 2 mM 2-mercaptoethanol), chelator (i.e.,., 0.1 to 0.25 mM EDTA), 75 to 200 mM (optionally 150 mM) monovalent salt (i.e KCl) and, optimally 5%, by volume, glycerol.

The fraction containing eluant is further purified by dialysis against an aqueous solution buffered to pH 5.5. to 6.5 (i.e., 10 to 20 mM sodium or potassium phosphate) and containing reducing agent (i.e., 1 to 2 mM 2-mercaptoethanol), chelator (i.e., 0.1 to 0.25 mM EDTA), 10 to 50 mM, (optimally 20 mM) of monovalent salt (i.e., KCl), protease inhibitor (i.e., 1 to 3 mM PMSF) and, optimally 5%, by volume, glycerol. It is essential that the pH of the buffered medium containing the active enzyme be changed from alkaline pH to acid pH by dialysis rather than by exclusion chromatography so as to avoid irreversible denaturation of the enzyme on the exclusion gel.

Additional interfering proteinaceous impurities or activities are removed from the dialyzed second fraction by contacting the latter with a weak cation exchange resin, e.g., carboxymethyl cellulose (CMC), preferably in a chromatographic column whereby the active enzyme is preferentially adsorbed. A fraction containing a portion of the active enzyme and a major protein contaminant is eluted from the CMC column with an aqueous medium buffered to pH 5.5. to 6.5, preferably to pH 6 (i.e., 10 to 20 mM sodium or potassium phosphate) and containing reducing agent (i.e., 1 to 2 mM 2-mercaptoethanol), chelator (i.e., 0.1 to 0.25 mM EDTA), 50 mM to 100 mM (optimally 75 mM) monovalent salt (i.e., KCl) and, optimally 5%, by volume, glycerol. Another fraction containing more of the active enzyme and lesser amounts of interfering impurities is eluted from the CMC column with the aqueous medium used to elute the second fraction but containing 100 to 200 mM (optimally 150 mM) monovalent salt (i.e., KCl).

The active enzyme containing the fractions from the above step are combined and diluted with an aqueous medium buffered at pH 6 (i.e., 10 to 20 mM sodium or potassium phosphate) containing reducing agent (i.e., 1 to 2 mM 2-mercaptoethanol), chelator (i.e., 0.1 to 0.25 mM EDTA) and, optimally 5%, by volume, glycerol to reduce the monovalent salt concentration (i.e., 75 mM KCl). The diluted active enzyme is essentially freed of all further interfering activities by preferential adsorption onto a polynucleotide covalently bonded to an inert matrix, e.g., deoxyoligo dT-cellulose (DT), preferably in a chromatographic column. The pure enzyme is eluted therefrom with an aqueous medium buffered to pH 8 to 9, preferably to pH 8.5. (i.e., 10 to 20 mM sodium or potassium phosphate buffer) and containing reducing agent (i.e., 1 to 2 mM 2-mercaptoethanol), chelator (i.e., 0.1 to 0.25 mM EDTA), 50 to 100 mM monovalent salt (i.e., KCl) and, optimally 5%, by volume, glycerol.

The substantially pure enzyme may be concentrated 25- to 50-fold from the elution medium by vacuum dialysis against a medium buffered to from pH 7.5 to 8.5 (i.e., 5 to 25 mM Tris.HCl) and containing reducing agent (i.e., 1 to 2 mM 2-mercaptoethanol), chelator (i.e., 0.1 to 0.25 mM EDTA), monovalent salt (i.e., 5 to 25 mM KCl) and, optimally 10%, by volume, glycerol. The concentrated enzyme, buffered at pH 7.5 to 8.5 and in 10% glycerol is stable for no less than 1 year at $-20°C$.

The active enzyme can be isolated from solution by adjusting the inert salt ionic strength of the concentrated eluant of from about 3.6M to about 7.2M, preferably about 4.8M and harvesting the thus precipitated enzyme.

EXAMPLE

Frozen shoots (30 Kg) are prepared from 12 liters of WF9xBear 38, waxy grain germinated for four days under running tap water at 20° C. and harvested to liquid nitrogen (utilizing a stainless steel gravel shaker) and stored in 100 g lots at −76°C. In 400 g batches the shoots are simultaneously thawed and ground in a one gallon, teflon-lined Waring blender to a fine slurry in 525 ml of freshly prepared and sterile medium H (100 mM Tris.HCl pH 8, 50 mM 2-mercaptoethanol, 0.1 mM ethylene diamine tetraacetic acid (EDTA), 5% glycerol and 1 mM phenylmethylsulfonylfluoride (PMSF). All media and glassware are sterilized before use. All subsequent operations are conducted at 4° C. unless stated otherwise. The homogenate is filtered through four layers of cheese cloth, wet with medium H and the remaining liquid expressed from the bolus of tissue with an orange juice squeezer. The filtrate is passed through two layers of miracloth, wet with medium H and the resulting filtrate immediately centrifuged at 40,000 RPM in a Beckman 50.2 rotor for 60 min. at 0° C. The supernatant fluid is decanted through miracloth, wet with medium H, and the pooled filtrate (430 ml) adjusted to pH 8 with NH$_4$OH. Additional PMSF is added to raise the final concentration to 2 mM and the solution is brought to 50% saturated (NH$_4$)$_2$SO$_4$ by dropwise addition of saturated (NH$_4$)$_2$SO$_4$ at pH 8, with stirring at 4° C. for 30 min. and the insoluble material harvested by centrifugation at 10,000 xg for 10 min. at 0° C. The supernatant fluid is discarded, the pellets drained and the lipid adhering to the tube walls removed. The pelleted material is resuspended in small aliquots of medium B (10 mM Tris.HCl pH 8, 1 mM 2-mercaptoethanol, 0.1 mM EDTA, 5% glycerol), pooled, brought to 50 ml and clarified by centrifugation at 5000 xg for 5 min. at 0° C.

The clarified supernatant fluid is excluded from Sephadex G 100 and the salt concentration adjusted by chromatography on a 2.6×66 cm column, equilibrated and eluted with 200 mM (NH$_4$)$_2$SO$_4$ in medium B at 1 ml/min. The excluded volume is pumped directly onto a 2.5×20 cm DEAE-cellulose (0.7 meq/mg) column previously equilibrated overnight with 200 mM (NH$_4$)$_2$SO$_4$ in medium B at 1 ml/min. The unadsorbed proteins are washed from the DEAE-cellulose column with 65 ml 200 mM (NH$_4$)$_2$SO$_4$ in medium B and brought to 40% saturation (NH$_4$)$_2$SO$_4$ by addition of crystalline ammonium sulfate. The slurry is stored at −76° C. until sufficient quantities are accumulated (equivalent to 1.6 kg of frozen shoots).

The salt slurry of unadsorbed proteins is thawed, pooled (360 ml), additional PMSF is added to a concentration of 1 mM (previously added PMSF degrades upon storage) and the insoluble material is harvested by centrifugation at 10,000 xg for 10 min. at 0° C. The supernatant fluid is discarded and the pelleted material is resuspended in 185 ml medium B. The resuspended material is clarified by centrifugation at 2000 xg for 5 min. at 0° C.

The clarified supernatant fluid is excluded from Sephadex G 50 and the salt exchanged and concentration adjusted by chromatography on a 5×48 cm column, equilibrated and eluted with 50 mM KCl in medium B at 2 ml/min. The excluded volume, as eluted from the Sephadex column, is pumped directly onto a 2.5×20 cm DEAE-cellulose (0.7 meq/ml) column previously equilibrated with 50 mM KCl in medium B. After washing away the unadsorbed proteins with 100 ml 50 mM KCL in medium B, the enzyme is eluted, stepwise, with 150 mM KCl in medium B at 1 ml/min. The eluted enzyme (20 ml) is dialyzed twice against 20 mM KCl in medium E (10 mM sodium phosphate buffer at pH 6.0, 1 mM mercaptoethanol, 0.1 mM EDTA and 5% glycerol) for 12 hr. The dialyzed enzyme is adsorbed to a carboxymethyl-cellulose (CMC) columns (2.5×10 cm) equilibrated with 20 mM KCl in medium E. After washing away the unadsorbed proteins with 100 ml 20 mM KCl im medium E, the adsorbed proteins are eluted in two steps. The first peak of active enzyme is eluted in 75 mM KCl in medium E and the second peak of enzyme of higher specific activity is eluted at 150 mM KCl in medium E. The eluted peaks are immediately combined, diluted with medium E to reduce the KCl concentration to 75 mM and adsorbed onto a deoxyoligo dT-cellulose column (1.2×5 cm) and washed with 35 ml 75 mM KCl in medium E. The active enzyme is eluted in medium buffered to pH 8.5 containing the components of medium E at 1 ml/min. in 10 ml and concentrated by vacuum dialysis.

The enzyme was precipitated by adjusting the inert salt ionic strength to 4.8M and harvesting the precipitated active enzyme as a pellet after centrifugation at 10,000 xg for 10 minutes.

It will be understood by those skilled in the art having been exposed to the principles of the present invention as set forth hereinabove that the broad concentration ranges for the various reagents utilized in the method of isolation of the enzyme include values which will result in the production of at least some enzyme, but that one may carry out the method operating somewhat outside those ranges with limited success with the costs attendant an inefficient operation. The appended claims, while setting forth the described broad ranges in the interests of adequately defining the invention, are intended to cover values which differ only insignificantly therefrom but which result in production of at least some enzyme. It will also be understood that all percentage values expressed herein are based on weight unless otherwise stated.

I claim:
1. A method of preparing ATP: polynucleotide adenylyltransferase enzyme in substantially pure form comprising the sequential steps;
   (a) homogenizing monocotyledonous plant tissue in an aqueous medium buffered to a mildly alkaline pH to solubilize said enzyme and separating isoluble material from said solution;
   (b) dissolving in the aqueous solution obtained in step (a) the minimum amount of soluble, inert salt necessary to precipitate substantially all of said enzyme and separating said precipitated enzyme from said solution;
   (c) dissolving said precipitated enzyme from step (b) in an aqueous medium buffered to a mildly alkaline pH;
   (d) removing from the solution produced in step (c) any low molecular weight cellular components dissolved therein and adjusting the inert salt ionic strength thereof to from about 0.45M to about 0.75M;
   (e) contacting the solution from step (d) with a weak anion exchange resin whereby nucleic acids, competing enzymic activities and proteinaceous impurities are chromatographically adsorbed thereby to the exclusion of said ATP enzyme;

(f) isolating said ATP enzyme following said chromatographic separation of step (e), dissolving said enzyme in an aqueous medium buffered to a mildly alkaline pH and adjusting the inert salt ionic strength thereof to from about 30 mM to about 75 mM;

(g) contacting the solution of step (f) with a weak anion exchange resin whereby said ATP enzyme is chromatographically adsorbed thereby to the exclusion of proteinaceous impurities;

(h) eluting the adsorbed enzyme from said resin and dialyzing the eluted fraction from step (g) against an aqueous solution buffered to a mildly acid pH and having an ionic strength of dissolved inert salt of from about 10 mM to about 30 mM;

(i) contacting said dialyzed fraction with a weak cation exchanger to chromatographically adsorb therefrom the ATP enzyme to the exclusion of proteinaceous impurities from which the adsorbed enzyme is separated after elution from said weak cation exchanger with an aqueous medium buffered to a mildly acid pH and having an inert salt ionic strength of from about 50 mM to about 200 mM;

(j) contacting said eluted fraction with a polynucleotide covalently bound to an inert matrix to chromatographically adsorb therefrom the ATP enzyme to the exclusion of proteinaceous impurities from which the adsorbed enzyme is separated after elution from said bound polynucleotide with an aqueous medium buffered to an alkaline pH and having an inert salt concentration of from about 50 mM to about 200 mM.

2. The method of claim 1 further comprising the step of concentrating the eluate from step (j) by vacuum dialysis against an aqueous medium buffered to an alkaline pH and having an inert salt ionic strength of from about 5 mM to about 25 mM.

3. The method of claim 1 wherein said plant tissue comprises young corn shoots.

4. The method of claim 3 wherein said young corn shoots are about 4 days old.

5. The method of claim 1 wherein said plant tissue is frozen and is homogenized and thawed simultaneously.

6. The method of claim 1 wherein in step (a) said aqueous medium contains a reducing agent in an amount effective to inhibit auto-oxidation of lignins and phenolic compounds in said plant tissue, an amount of chelating agent effective to chelate any heavy metals present in said plant tissue and a protease inhibitor.

7. The method of claim 6 wherein in said medium of step (a) said reducing agent is 2-mercaptoethanol and is present in a concentration of from about 25 mM to about 75 mM, said chelating agent is EDTA and is present in a concentration of from about 0.05 mM to about 0.25 mM, said protease inhibitor is phenylmethylsulfonylfluoride and is present in a concentration of from about 0.5 mM to about 3 mM and wherein said medium is buffered to a pH of about 8 by the presence of Tris.HCl in a concentration of about 100 mM.

8. The method of claim 6 wherein said medium of step (a) additionally contains 5%, by volume, of glycerol.

9. The method of claim 1 wherein said insoluble material is separated from said medium in step (a) by sequential filtration and centrifugation.

10. The method of claim 1 wherein said soluble, inert salt in step (b) is ammonium sulfate.

11. The method of claim 10 wherein sufficient ammonium sulfate is dissolved in said aqueous medium to produce an approximately 50%, by weight, saturated solution thereof whereby to precipitate said enzyme.

12. The method of claim 11 wherein said ammonium sulfate is added to said aqueous medium in step (b) in the form of a saturated solution thereof.

13. The method of claim 1 wherein said precipitate produced in step (b) is separated from said aqueous medium by sequential filtration and centrifugation.

14. The method of claim 1 wherein said aqueous medium of step (c) contains an amount of a reducing agent effective to inhibit the auto-oxidation of any lignins and phenolic compounds present therein and an amount of a chelating agent effective to chelate any heavy metals present therein.

15. The method of claim 14 wherein said aqueous medium of step (c) said reducing agent is 2-mercaptoethanol and is present in a concentration of about 1 mM and said chelating agent is EDTA and is present in a concentration of about 0.1 mM.

16. The method of claim 14 wherein said aqueous medium of step (c) additionally contains about 5%, by volume, of glycerol.

17. The method of claim 1 further including the step of clarifying the solution produced by step (c) by centrifugation.

18. The method of claim 1 wherein said inert salt the concentration of which is adjusted in step (d) is ammonium sulfate and said cellular components removed in step (d) have a molecular weight lower than about 100,000.

19. The method of claim 18 wherein said low molecular weight cellular components are removed from and the inert salt concentration in said solution is adusted by contacting said solution in step (d) with a dextran gel previously equilibrated and eluted with an aqueous solutin buffered to pH 8 and having a concentration of reducing agent effective to inhibit the auto-oxidation of any lignins and phenolic compounds present therein, a concentration of chelating agent effective to chelate any heavy metal present therein and an ionic strength of inert salt of about 0.6M.

20. The method of claim 19 wherein said equilibration and elution medium contains 10 mM Tris.HCl, 1 mM 2-mercaptoethanol, 0.1 mM EDTA, 5% glycerol and 200 $(NH_4)_2SO_4$.

21. The method of claim 19 wherein said dextran gel is Sephandex G 100.

22. The method of claim 1 wherein said anion exchange resin in step (e) is diethylaminoethyl-cellulose and from which a non-adsorbed fraction containing ATP enzyme is eluted with an aqueous medium buffered to a pH of about 8 and having an inert salt ionic strength of about 0.6M.

23. The method of claim 22 wherein said enzyme containing first fraction is eluted from siad diethylaminoethyl-cellulose in step (d) with a solution additionally containing an amount of reducing agent effective to inhibit the auto-oxidation of any lignins and phenolic compounds present therein and an amount of chelating agent effective to chelate any heavy metals present therein.

24. The method of claim 23 wherein said enzyme containing first fraction is eluted from said diethylaminoethyl-cellulose with a solution containing 10 mM Tris.HCl, 1 mM 2-mercaptoethanol, 0.1 mM EDTA, 5%, by volume, glycerol and 200 mM $(NH_4)_2SO_4$.

25. The method of claim 22 wherein said aqueous solution in step (f) additionally contains an amount of reducing agent effective to inhibit the auto-oxidation of any lignins and phenolic compounds present therein and an amount of chelating agent effective to chelate any heavy metals present therein.

26. The method of claim 25 wherein said aqueous solution of step (f) contains 10 mM sodium phosphate, 1 mM 2-mercaptoethanol, 0.1 mM EDTA, 5%, by volume, glycerol and 20 mM KCl.

27. The method of claim 1 wherein said elution medium of step (i) additionally contains an amount of reducing agent effective to inhibit the auto-oxidation of any lignins and phenolic compounds present therein and an amount of chelating agent effective to chelate any heavy metals present therein.

28. The method of claim 27 wherein said elution medium of step (g) contains 10 mM sodium phosphate, 1 mM 2-mercaptoethanol, 0.1 mM EDTA, 5%, by volume, glycerol and 75 mM KCl.

29. The method of claim 1 wherein said elution medium of step (j) additionally contains an amount of reducing agent effective to inhibit the auto-oxidation of any lignins and phenolic compounds present therein and an amount of chelating agent effective to chelate any heavy metals present therein.

30. The method of claim 29 wherein said elution medium of step (j) contains 10 mM sodium phosphate, 1 mM 2-mercaptoethanol, 0.1 mM EDTA, 5%, by volume, glycerol and 75 mM KCl.

31. The method of claim 1 wherein said enzyme is isolated from said eluant in step (j) by adjusting the inert salt ionic strength of said eluant to fromabout 3.6M to about 7.2M to precipitate the enzyme and separating the precipitated enzyme therefrom.

* * * * *

UNITED STATES PATENT AND TRADEMARK OFFICE
CERTIFICATE OF CORRECTION

PATENT NO. : 4,695,550
DATED : September 22, 1987
INVENTOR(S) : RUSTY J. MANS

It is certified that error appears in the above-identified patent and that said Letters Patent is hereby corrected as shown below:

Claim 19, line 43, change "metal" to --metals--;

Claim 23, line 58, change "siad" to --said--;

Claim 31, line 17, change "fromabout" to --from about--.

Signed and Sealed this

Ninth Day of February, 1988

Attest:

DONALD J. QUIGG

Attesting Officer      Commissioner of Patents and Trademarks